(12) United States Patent
Falck et al.

(10) Patent No.: US 10,720,240 B2
(45) Date of Patent: Jul. 21, 2020

(54) CONTEXT DETECTION FOR MEDICAL MONITORING

(71) Applicant: KONINKLIJKE PHILIPS N.V., Eindhoven (NL)

(72) Inventors: Thomas Falck, Aachen (DE); Teun Van Den Heuvel, Eindhoven (NL); Esther Marjan Van Der Heide, Hertogenbosch (NL); Adrienne Heinrich, Den Bosch (NL); Yingrong Xie, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 298 days.

(21) Appl. No.: 15/551,741

(22) PCT Filed: Feb. 21, 2016

(86) PCT No.: PCT/EP2016/053616
§ 371 (c)(1),
(2) Date: Aug. 17, 2017

(87) PCT Pub. No.: WO2016/135069
PCT Pub. Date: Sep. 1, 2016

(65) Prior Publication Data
US 2018/0014790 A1    Jan. 18, 2018

(30) Foreign Application Priority Data

Feb. 26, 2015    (EP) ..................................... 15156643

(51) Int. Cl.
*G16H 50/20*        (2018.01)
*A61B 5/00*         (2006.01)
(Continued)

(52) U.S. Cl.
CPC ........... *G16H 50/20* (2018.01); *A61B 5/0024* (2013.01); *A61B 5/0077* (2013.01);
(Continued)

(58) Field of Classification Search
CPC ...... G16H 50/20; G16H 40/63; A61B 5/7264; A61B 5/02055; A61B 5/746;
(Continued)

(56) References Cited

U.S. PATENT DOCUMENTS

2010/0312297  A1*  12/2010  Volpe ................... A61B 5/0404
                                                                      607/6
2014/0081654  A1    3/2014   Bechtel
(Continued)

FOREIGN PATENT DOCUMENTS

EP         2767232         8/2014
WO      2011/116340        9/2011
(Continued)

OTHER PUBLICATIONS

M. Görges, et al., "Improving Alarm Performance in the Medical Intensive Care Unit Using Delays and Clinical Context", Anesthesia and Analgesia, 2009.
(Continued)

*Primary Examiner* — Ryan Sherwin

(57) ABSTRACT

There is provided a context detection apparatus for use with a medical monitoring device arranged to measure a physiological characteristic of a subject. The context detection apparatus comprises at least one context sensor comprising a camera; and a processing unit. The processing unit is arranged to receive image data acquired by the camera from the at least one context sensor; analyze the received image data to generate a plurality of different types of context information; wherein each type of context information comprises information which relates to a factor capable of
(Continued)

influencing measured values of the physiological characteristic and which is not measurable by the medical monitoring device; and output a signal to the medical monitoring device based on the generated context information. The processing unit is arranged to analyze the received image data by detecting features in the received image data; and classifying each detected feature as relating to a particular one of the plurality of types of context information.

3 Claims, 5 Drawing Sheets

(51) Int. Cl.
| | |
|---|---|
| *A61B 5/11* | (2006.01) |
| *G16H 40/63* | (2018.01) |
| *A61B 5/0205* | (2006.01) |
| *G06F 19/00* | (2018.01) |
| *A61B 5/024* | (2006.01) |
| *A61B 5/1455* | (2006.01) |
| *A61B 5/0402* | (2006.01) |
| *A61B 5/01* | (2006.01) |
| *A61B 5/0215* | (2006.01) |

(52) U.S. Cl.
CPC ........ *A61B 5/02055* (2013.01); *A61B 5/1113* (2013.01); *A61B 5/1116* (2013.01); *A61B 5/1118* (2013.01); *A61B 5/1128* (2013.01); *A61B 5/7203* (2013.01); *A61B 5/7264* (2013.01); *A61B 5/746* (2013.01); *G06F 19/321* (2013.01); *G16H 40/63* (2018.01); *A61B 5/01* (2013.01); *A61B 5/0215* (2013.01); *A61B 5/02416* (2013.01); *A61B 5/0402* (2013.01); *A61B 5/14551* (2013.01); *A61B 5/7282* (2013.01); *A61B 2560/0247* (2013.01); *A61B 2576/00* (2013.01)

(58) Field of Classification Search
CPC ... A61B 5/1128; A61B 5/0077; A61B 5/1118; A61B 5/1113; A61B 5/0024; A61B 5/7203; A61B 5/1116; A61B 2576/00; A61B 5/0215; A61B 2560/0247; A61B 5/14551; A61B 5/02416; A61B 5/0402; A61B 5/01; A61B 5/7282; G06F 19/321
See application file for complete search history.

(56) References Cited

U.S. PATENT DOCUMENTS

2014/0235976 A1* 8/2014 Bresch .............. A61B 5/14551
  600/323
2014/0267718 A1 9/2014 Govro

FOREIGN PATENT DOCUMENTS

| WO | 2011/129817 | 10/2011 |
|---|---|---|
| WO | 2012/104476 | 8/2012 |
| WO | 2014/140978 | 9/2014 |

OTHER PUBLICATIONS

M. Imhoff, et al., "The crying wolf: still crying?", Anesthesia and Analgesia, 2009.
Littner, et al., "Practice Parameters for the Role of Actigraphy in the Study of Sleep and Circadian Rhythms: An Update, for 2002"; Sleep, vol. 26, Issue 3, May 1, 2003, pp. 337-341.
Ancoli-Israel, et al., "The Role of Actigraphy in the Study of Sleep and Circadian Rhythms"; Sleep, vol. 26, Issue 3, May 1, 2003, pp. 342-392.
Ji, et al., "Real-Time Nonintrusive Monitoring and Prediction of Driver Fatigue", IEEE Trans. Vehicular Technology. vol. 53, No. 4, Jul. 2004, pp. 1052-1068.
Heinrich, et al., "Body movement analysis during sleep based on video motion estimation"; 15th IEEE International Conference on e-Health Networking Applications and Services (Healthcom), 2013.
Orazio, et al., "A Visual Approach for Driver Inattention Detection", Pattern Recognition, vol. 40, Jan. 2007, pp. 2341-2355.
Hsu, et al., "Face Detection in Color Images", IEEE Trans. Pattern Analysis and Machine Intelligence. vol. 24, No. 5, May 2002, pp. 696-706.
Viola, et al., "Robust real-time face detection", Proc. ICCV, pp. 1254-1259 (2001).
Comaniciu, et al., "Real-time tracking of non-rigid objects using mean shift", IEEE CVPR, pp. 142-149, Jun. 2000.
Trinh, et al., "Efficient UAV video event summarization", Pattern Recognition (ICPR), 2012 21st International Conference on, on pp. 2226-2229, vol. Issue: , Nov. 11-15, 2012.
Liu, et al., "An Adapting to Light Change Pixel Layer Based Background Model for Moving Objects Detection in a Dynamic Scene," 2012 11th International Symposium on Distributed Computing and Applications to Business, Engineering & Science.

* cited by examiner

US 10,720,240 B2

CONTEXT DETECTION FOR MEDICAL MONITORING

CROSS REFERENCE TO RELATED APPLICATIONS

This application is the U.S. National Phase application under 35 U.S.C. § 371 of International Application No. PCT/EP2016/053616, filed Feb. 21, 2016, published as WO 2016/135069 on Sep. 1, 2016, which claims the benefit of European Patent Application Number 15156643.7 filed Feb. 26, 2015. These applications are hereby incorporated by reference herein.

TECHNICAL FIELD OF THE INVENTION

The invention relates to a context detection method and apparatus for use in medical monitoring, and in particular relates to a context detection apparatus for use with a medical monitoring device arranged to measure a physiological characteristic of a subject.

BACKGROUND TO THE INVENTION

Patient monitoring is an important part of healthcare. A major challenge in patient monitoring is to achieve high sensitivity combined with high specificity, in other words the ability to reliably detect events or features of interest whilst minimizing false positive detections.

Many medical monitoring devices are configured to generate alarms in response to a detected change in the status of the patient (subject), the purpose of which is to indicate to medical staff that the subject may need urgent attention. However, various circumstances can lead to an alarm being generated when the subject is not in need of attention, and these alarms are therefore considered to be false alarms. Studies show that the majority of false alarms are caused by nursing care (e.g. activities such as suctioning, repositioning, oral care, and/or washing of the subject) or by voluntary movements or interactions with the monitoring equipment by the subject.

False alarms are undesirable because they waste the time of healthcare professionals in responding to them, and can create "alarm fatigue", in which caregivers become desensitized to alarms and can begin to ignore or even disable the alarm generation functions of medical monitoring devices. The generation of an excessive number of false alarms by medical monitoring equipment can therefore jeopardize subject safety.

There is therefore a need for a system which can reduce the number of false alarms generated by medical monitoring systems, without missing genuine alarms.

SUMMARY OF THE INVENTION

According to a first aspect of the invention, there is provided a context detection apparatus for use with a medical monitoring device arranged to measure a physiological characteristic of a subject. The context detection apparatus comprises at least one context sensor comprising a camera, and a processing unit. The processing unit is arranged to receive image data acquired by the camera from the at least one context sensor; analyze the received image data to generate a plurality of different types of context information; and output a signal to the medical monitoring device based on the generated context information. Each of the types of context information comprises information which relates to a factor capable of influencing measured values of the physiological characteristic and which is not measurable by the medical monitoring device. The processing unit is arranged to analyze the received image data by detecting features in the received image data; and classifying each detected feature as relating to a particular one of the plurality of types of context information.

In some embodiments the generated context information comprises one or more of:
information relating to the movement of a body part of the subject;
information relating to the posture of a subject;
information relating to the activity of a subject;
information relating to the location of a subject;
information relating to the position and/or movement of a medical device or part thereof;
information relating to one or more persons in the vicinity of the subject;
information relating to the environment of the subject.

In some embodiments the processing unit comprises a memory containing one or more predefined signatures, each predefined signature relating to a particular type of feature, and wherein the processing unit is arranged to detect features by comparing the received image data to the one or more predefined signatures. In some embodiments the processing unit comprises a memory containing rules specifying a relationship between each of multiple types of feature and one or more types of context information.

In some embodiments the output signal comprises one or more of:
the generated context information;
a summary of the generated context information;
relevance information associated with the generated context information;
confidence information associated with the generated context information
time information associated with the generated context information.

In some such embodiments the at least one context sensor comprises a plurality of cameras. In some embodiments the at least one context sensor comprises an infrared (IR) camera. In some embodiments the at least one context sensor comprises at least microphone and the received data comprises audio data.

There is also provided, according to a second aspect of the invention, a medical monitoring device. The medical monitoring device comprises at least one sensor arranged to obtain measured values of a physiological characteristic of a subject; and a processing unit. The processing unit is arranged to receive measured values of the physiological characteristic from the at least one sensor; receive a context signal from a context detection apparatus; and select an action to perform. The action is selected in dependence on the received context signal and on the received measured values. The signal is based on a plurality of different types of context information generated by the context detection apparatus. Each of the types of context information comprises information which relates to a factor capable of influencing measured values of the physiological characteristic and which is not measurable by the medical monitoring device.

In some embodiments the action is selected from a set comprising one or more of:
generating an alarm;
not generating an alarm;
altering an alarm generation criterion;
suppressing an alarm generated in response to the received measured values;

altering a parameter relating to the emission of a generated alarm;

ignoring one or more of the received measured values;

flagging one or more of the received measured values as potentially unreliable;

generating a context alarm.

There is also provided, according to a third aspect of the invention, a medical monitoring system comprising a context detection apparatus according to the first aspect of the invention; and a medical monitoring device according to the second aspect of the invention. The medical monitoring device is arranged to receive context signals from the context detection apparatus.

There is also provided, according to a fourth aspect of the invention, a method for use in monitoring a physiological characteristic of a subject using a medical monitoring device. The method comprises receiving image data acquired by a camera from at least one context sensor comprising the camera; analyzing the received image data to generate a plurality of different types of context information; and outputting a context signal to the medical monitoring device based on the generated context information. Each of the types of context information comprises information which relates to a factor capable of influencing measured values of the physiological characteristic and which is not measurable by the medical monitoring device. The analyzing comprises detecting features in the received image data; and classifying each detected feature as relating to a particular one of the plurality of types of context information.

In some embodiments the method further comprises comparing each type of generated context information to at least one predefined criterion; and assigning a relevance value to each type of generated context information based on the comparing.

In some embodiments the method comprises measuring multiple physiological characteristics using the medical monitoring, and the at least one predefined criterion is specific to a particular type of context information and to a particular physiological characteristic. In some such embodiments assigning a relevance value to each type of generated context information comprises assigning a relevance value in respect of each of the multiple physiological characteristics to each type of generated context information. In some embodiments the at least one predefined criterion comprises a set of conditions, which must all be met by a given item of context information in order for a positive relevance value to be assigned to that context information.

In some embodiments the method further comprises receiving, by a medical monitoring device, measured values of a physiological characteristic from a sensor; receiving, by the medical monitoring device, the context signal; and selecting, by the medical monitoring device, an action to perform. The action is selected in dependence on the received context signal and on the received measured values.

There is also provided, according to a fifth aspect of the invention, a computer program product comprising computer readable code embodied therein, the computer readable code being configured such that, on execution by a suitable computer or processing unit, the computer or processing unit performs at least part of the method of the fourth aspect of the invention.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Context-awareness is one way in which the number of false alarms generated by a medical monitoring device can be reduced. The "context" of a measurement (e.g. of a physiological characteristic of a subject) includes any factor which can influence the correct acquisition of measurement values or the interpretation thereof. Such factors can include (but are not limited to) movement of the subject and/or the measuring sensor during the measuring process, attachment location of a sensor, other people (e.g. caregivers or family members) or objects interacting with the subject during the measuring process, and environmental factors (e.g. time of day, temperature, background noise level). Contextual factors are generally not directly related to the physiological characteristic being measured, but instead can influence the measurement results indirectly, e.g. by causing a non-clinically relevant change in the measured physiological characteristic, or by affecting the functioning of the measurement apparatus. Knowledge of the measurement context can therefore be useful in interpreting the measured values, leading to improved monitoring quality and potentially enabling the automation of various diagnosis or treatment processes. It can also be used to prevent the generation of alarms in situations where context information indicates that an abnormal measured value is not of concern (e.g. because the subject moved whilst the measurement was being acquired, or tampered with the monitoring equipment).

Figure 1:
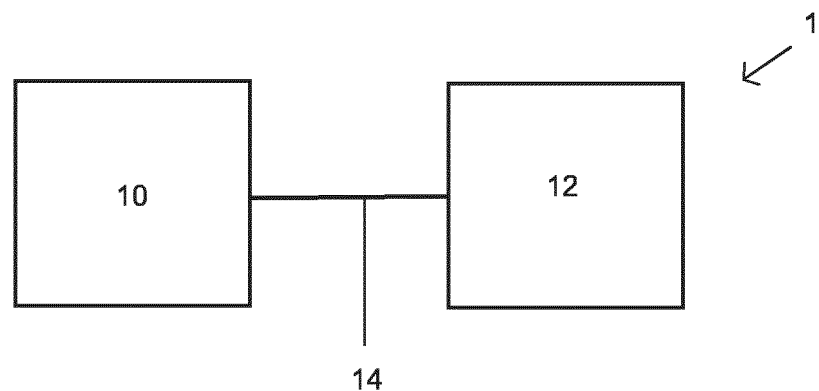
FIG. 1 is an illustration of a context detection apparatus according to a general embodiment of the invention.

FIG. 1 shows a context detection apparatus 1 for use with a medical monitoring device arranged to measure a physiological characteristic of a subject, according to an embodiment of the invention. The context detection apparatus 1 has a context sensor 10 and a processing unit 12. The context sensor 10 and the processing unit 12 are in communication via a communications link 14, which may be wired or wireless. In some embodiments the context sensor 10 and the processing unit 12 are provided in the same device housing. In alternative embodiments the context sensor 10 and the processing unit 12 are provided as separate devices.

The context sensor 10 is arranged to acquire sensor data and to send the acquired sensor data to the processing unit 12 by means of the communications link 14. In some embodiments the context sensor comprises a camera. Alternatively, the context sensor may comprise an accelerometer, a microphone, a heat sensor, a proximity sensor, or any other type of sensing device arranged to acquire data. In some embodiments the context detection apparatus device 1 comprises a plurality of context sensors. In such embodiments the plurality of context sensors may all be of the same type, or they may be of a variety of different types. It is generally expected that the context detection device will acquire data which is not measurable by the medical monitoring device with which the context detection apparatus is intended to be used. For the purposes of the application "not measurable" is intended to include "not arranged to be measured by". For example, a medical monitoring device arranged to use a camera to monitor movements of a subject's chest is not arranged to detect the movement of caregivers within the camera's field of view. As such, the presence of caregivers in the vicinity of the subject is considered not measurable by that medical monitoring device.

The processing unit 12 is arranged to receive data from the context sensor 10 (i.e. by means of the communications link 14). The processing unit 12 is further arranged to analyze the received data to generate one or more types of context information. Context information can comprise any information which could influence the measured value of a physiological characteristic of the subject, or the interpretation of that measurement. Some examples of types of context information are:

Information relating to the movement of a body part of the subject;
Information relating to the location of the subject;
Information relating to the posture of a subject;
Information relating to the activity of a subject;
Information relating to the position and/or movement of a part (e.g. a sensor) of a medical device;
Information relating to other persons in the vicinity of the subject, for example their number, identity, proximity to the subject, activity level, etc.
Information relating to the environment of the subject, for example time of day, light level, temperature, background noise level, etc.

It is generally expected that a given item of context information will take the form of a value. In some cases a given item of context information will comprise a numerical value, e.g. a distance in meters, a speed in m/s, a noise level in decibels, etc. In some cases a given item of context information will comprise a non-numerical value, e.g. in some embodiments an item of context information relating to time of day can take the values "day" or "night".

In some embodiments the processing unit 12 is arranged to generate context information by detecting features in the data received from the context sensor 10, and classifying each detected feature as relating to a particular type of context information. In some embodiments the processing unit comprises a memory containing one or more predefined signatures, each predefined signature relating to a particular type of feature. In some such embodiments the processing unit is arranged to detect features by comparing the received data to the one or more predefined signatures. In some embodiments the processing unit 12 comprises a memory containing rules specifying a relationship between each of multiple types of feature and one or more types of context information. It will be appreciated that any suitable data analysis techniques known in the art can be used in the detection and/or classification of features.

In some embodiments the processing unit 12 is arranged to generate a plurality of different types of context information based on a single received data signal. In some embodiments the processing unit 12 is arranged to generate a plurality of different types of context information based on data acquired by a single sensor, or based on a single type of sensor data (which may have been acquired by multiple sensors of the same type). For example, in some embodiments in which the context sensor 10 comprises a microphone, the processing unit is arranged to detect and quantify a background noise level, the presence of other persons in the vicinity of the subject (e.g. by detecting and analyzing footsteps in the received signal, and or voices in the received signal) and a distress level of the subject (e.g. by detecting and analyzing vocalizations of the subject in the received signal). Advantageously, generating multiple types of context information from a single type of sensor data means that a complete or near complete picture of the context in which a given physiological measurement has been acquired can be obtained, with minimal cost and obtrusiveness.

In some embodiments the processing unit 12 is further arranged to compare each type of generated context information to at least one predefined criterion. This can enable the relevance of the context information to be more easily determined. The at least one predefined criterion may be specific to the type of context information. For example, in some embodiments one of the types of generated context information comprises a distance from the subject to a person in the vicinity of the subject (in other words, a proximity of a non-subject person to the subject). In some such embodiments the distance is compared to a predefined threshold, and the context information is determined to be relevant or not based on the comparison. For example, in some embodiments distances exceeding the threshold are determined to be not relevant (i.e. because the person is too far from the subject to have a significant influence on their physiological characteristics) whereas distances which are less than or equal to the threshold are determined to be relevant.

In some embodiments the at least one predefined criterion comprises a plurality of thresholds. Thus, in the distance example, in some embodiments distances exceeding an upper threshold are determined to be not relevant, distances between the upper threshold and a lower threshold are determined to have a medium relevance, and distances less than the lower threshold are determined to have a high relevance.

In some embodiments the at least one predefined criterion comprises a set of conditions, which must all be met by a given item of context information in order for the context information to be determined to be relevant. In some embodiments the set of conditions comprises a time-based condition and a value-based condition (for example the distance thresholds described above are value-based conditions, because whether or not the context information meets the condition depends on the value of the context information itself). A time-based condition may, for example, specify a minimum amount of time for which the context information has consistently met a value-based condition in order for the most recent context information to be determined to be relevant. Providing a time-based condition can be advantageous because some contextual factors may need to be consistently present for a while before they start to have a measurable effect on the subject's physiological characteristics. In some embodiments the set of conditions comprises a plurality of value-based conditions. For example, in one such embodiment the presence of a person in the vicinity of the subject is only determined to be relevant if they are within a predefined minimum distance of the subject and if they identified to be a certain type of person, e.g. a nurse.

In some embodiments at least one predefined criterion is defined in respect of each of the one or more types of context information, for each of multiple measured physiological characteristics. For example, consider a subject for whom a photoplethysmogram (PPG) is being obtained using a finger-mounted pulse oximeter and a blood pressure reading is being obtained using an arterial catheter. In this case, movement of the subject's hand to which the pulse oximeter is attached will affect the obtained PPG. However; it is less likely that the PPG measurements will be affected by the presence of another person in the vicinity of the subject. By contrast, the subject's blood pressure could be affected by the presence of another person (e.g. if it causes the subject to become stressed) but is unlikely to be affected by the subject moving a body part. Therefore, a PPG-hand movement criterion and a blood pressure-hand movement criterion can be defined separately such that only a small amount of hand movement is required to meet the PPG-hand movement criterion, whereas a large amount of hand movement (i.e. large enough to dislodge the catheter or indicate that the subject is in distress) is required to meet the blood pressure-hand movement criterion. Similarly, a PPG-proximity criterion and a separate blood pressure-proximity criterion can be defined. It will be appreciated that these considerations can be applied in respect of any measured physiological characteristics.

In some embodiments the processing unit 12 includes a machine learning module, configured to use standard machine learning techniques to identify or generate rules, relationships, etc. for the relevance of context data. In some such embodiments the machine learning module is configured to apply machine learning techniques to historical data, e.g. historical context data, historical physiological measurement data, and/or historical relevance information. In some such embodiments the processing unit 12 is arranged to generate relevance information based on rules or relationships generated or identified by the machine learning module.

In some embodiments the processing unit 12 is arranged to generate relevance information associated with each of the types of generated context information based on the results of the comparing. Such relevance information may comprise, for example, a determination of whether a given type of context information is relevant or not relevant. In some embodiments the relevance information comprises a relevance value (which may, for example, take the form of a relevant/not relevant indication, a numerical score, and/or a non-numerical relevance level). In some embodiments the relevance information comprises a relevance value in respect of each of the one or more types of context information, for each of multiple measured physiological characteristics, which preferably include the physiological characteristics being measured by a medical monitoring device with which the context detection apparatus implementing the method is in communication. For example, context information comprising a background noise level may be determined to be relevant to measured blood pressure but not relevant to measured body temperature. Alternatively or additionally, context information comprising a background noise level may be determined to have a first relevance level or score in respect of measured blood pressure and a second relevance level or score in respect of measured body temperature.

In some embodiments the processing unit 12 is arranged to generate confidence information associated with each of the types of generated context information. Such confidence information can indicate, e.g., a level of certainty that the generated context information is correct/accurate. For example, in a case where the context sensor comprises a camera, it is possible that a caregiver standing close to the subject could block the camera's view of another feature of interest, such as a sensor. When this occurs, context information relating to the other feature from the time during which it was not visible to the camera will have a reduced level of certainty compared with at times when the other feature was visible. It will be appreciated that, in this case, the level of certainty will decrease the longer the other feature remains obscured. In some embodiments the generated confidence information comprises a determination of whether a given item of context information is reliable or not reliable. In some embodiments the confidence information comprises a confidence value (which may, for example, take the form of a reliable/not reliable indication, a numerical score, and/or a non-numerical confidence level). In some embodiments the confidence information comprises a confidence value. Various suitable techniques for generating confidence information are known in the art.

In some embodiments the processing unit 12 is arranged to generate time information associated with each of the types of generated context information. In some embodiments the time information is generated based on a timestamp of the data received from the context sensor. The generated time information may, for example, indicate a time at which (or a time period during which) the context data used to generate the context information was acquired.

The processing unit 12 is further arranged to output a signal to a medical monitoring device (not shown) based on the generated context information, e.g. by means of a communications functionality of the processing unit 12. In some embodiments the processing unit 12 comprises a port to which a communications cable can be connected, to enable a wired communications link to be established between the processing unit 12 and the medical monitoring device. In some embodiments the processing unit 12 comprises or is connected to a wireless transmitter, to enable a wireless communications link to be established between the processing unit 12 and the medical device. In some embodiments the communication between the context detection apparatus 1 and the medical monitoring device is effected via a hospital network.

In some embodiments the signal comprises the one or more types of generated context information, e.g. values for a background noise level, a distance between a person and the subject, speed of movement of a body part of the subject, etc. In some embodiments the signal comprises relevance information associated with each of the types of generated context information. In some embodiments the signal contains time information associated with each of the types of generated context information.

Advantageously, the medical monitoring device which receives the signal can use it to interpret the significance of acquired physiological measurements and to adjust its response to those measurements. For example, when the signal indicates that a movement of a subject's hand which is relevant to PPG measurements has occurred or is occurring, the medical monitoring device can perform an appropriate action. In some embodiments in which the received signal does not contain relevance information, the medical monitoring device is arranged to generate relevance information using a process the same as or similar to the process described above in relation to the context detection apparatus 1. The appropriate action may comprise, for example, one or more of: generating an alarm; not generating an alarm; altering an alarm generation criterion; suppressing an alarm generated in response to the PPG measurements acquired during the movement; altering a parameter relating to the emission of a generated alarm; redirecting a generated alarm; ignoring or discarding the PPG measurements acquired during the movement, flagging the PPG measurements acquired during the movement as invalid or potentially unreliable.

Figure 2:
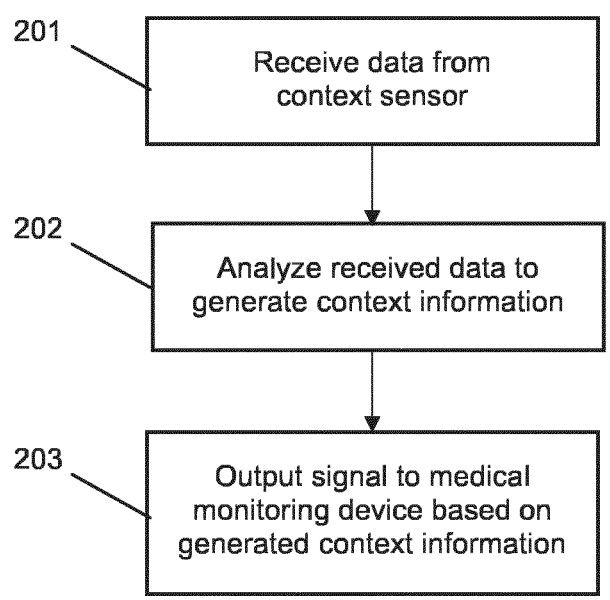
FIG. 2 is flow chart illustrating a method for use in monitoring a physiological characteristic of a subject using a medical monitoring device, according to a general embodiment of the invention.

FIG. 2 shows an example of a method for use in monitoring a physiological characteristic of a subject using a medical monitoring device, which can be implemented by the context detection apparatus 1. In a first step 201 context data is received, e.g. by the processing unit 12, from a context sensor, e.g. the context sensor 10. In some embodiments the context data is received as a continuous stream. In some embodiments the context data is received periodically. In some embodiments the context data is received in response to a request previously sent to the context sensor 10. In some embodiments the context data has been time-stamped at the time of its generation by the context sensor. In some embodiments the context data is time-stamped at the time of its receipt, e.g. by the processing unit 12.

In step 202 the received context data is analyzed, e.g. by the processing unit 12, to generate one or more types of context information. In some embodiments the analyzing comprises detecting patterns and/or features in the received context data. In some embodiments the analyzing comprises determining whether or not at least one predefined criterion is met. In some examples signatures and/or patterns associated with features of interest (such as a particular body part, a non-subject person, a sensor device, etc.) are stored in a memory associated with the processing unit 12, and the analyzing comprises comparing detected patterns/features with the stored signatures/patterns. In some embodiments the received context data is analyzed at a particular instant in time (i.e. the analysis is static). In some embodiments the analysis is performed on received context data covering a time period (i.e. the analysis is dynamic). In some embodiments the analyzing comprises tracking a detected feature over a time period. Any suitable known signal analysis and feature extraction techniques may be used in the performance of step 202.

In some embodiments an optional step of generating relevance information associated with a given item of context information is performed. In some embodiments the relevance information may take the form described above in relation to the operation of processing unit 12. In some embodiments an optional step of generating time information associated with a given item of context information is performed. In some embodiments the relevance information may take the form described above in relation to the operation of processing unit 12.

In some embodiments the context data is deleted following the completion of step 202. Advantageously, this can prevent or limit any impact on the subject's privacy.

In step 203 a signal is output (e.g. by the processing unit 12) to a medical monitoring device based on the one or more types of generated context information. The signal may be output using a wired or wireless communications link to the medical monitoring device. In some embodiments the signal is output continuously, in real-time or near-real time. In such embodiments, preferably the delay between the receipt of the context data and the output of the signal is less than the processing time required by the patient monitor for the generation of an alarm on the basis of a given physiological measurement. In some preferred embodiments the delay between the receipt of the context data and the output of the signal is less than one second.

In some embodiments the signal contains the one or more types of generated context information. In some embodiments the signal contains a summary of the one or more types of generated context information. In some embodiments the signal contains only types of context information which are associated with a positive relevance value in respect of at least one physiological characteristic measured by the medical monitoring device. In some embodiments the signal contains relevance information associated with each item of context information. In some embodiments the signal contains confidence information associated with each item of context information. In some embodiments the signal contains time information associated with each item of context information. Tables 1a-c show examples of items of context information, together with associated time, relevance and confidence information, included in a signal output by the context detection apparatus 1 to a medical monitoring device.

TABLE 1a

First example item of context information and associated time, confidence and relevance information.

| | |
|---|---|
| Context type | Movement of subject's left hand |
| Time | 10:03:25-10:03:26 |
| Value | 1.2 m/s |
| Confidence | Medium |
| Relevance: PPG | Relevant |
| Relevance: Heart rate | Not relevant |
| Relevance: Blood pressure | Not relevant |
| Relevance: Body temperature | Not relevant |

TABLE 1b

Second example item of context information and associated time, confidence and relevance information.

| | |
|---|---|
| Context type | Proximity of non-subject person |
| Time | 15:27:41 |
| Value | 0.5 m |
| Confidence | High |
| Relevance: Heart rate | Medium relevance |
| Relevance: Blood pressure | Medium relevance |
| Relevance: Body temperature | No relevance |
| Relevance: Thoracic bioimpedance | No relevance |

TABLE 1c

Third example item of context information and associated time, confidence and relevance information.

| | |
|---|---|
| Context type | Background noise level |
| Time | 11:15:02 |
| Value | 70 dB |
| Confidence | High |
| Relevance: Heart rate | Low relevance |
| Relevance: Blood pressure | Medium relevance |
| Relevance: Body temperature | No relevance |
| Relevance: Thoracic bioimpedance | No relevance |

Figure 3:
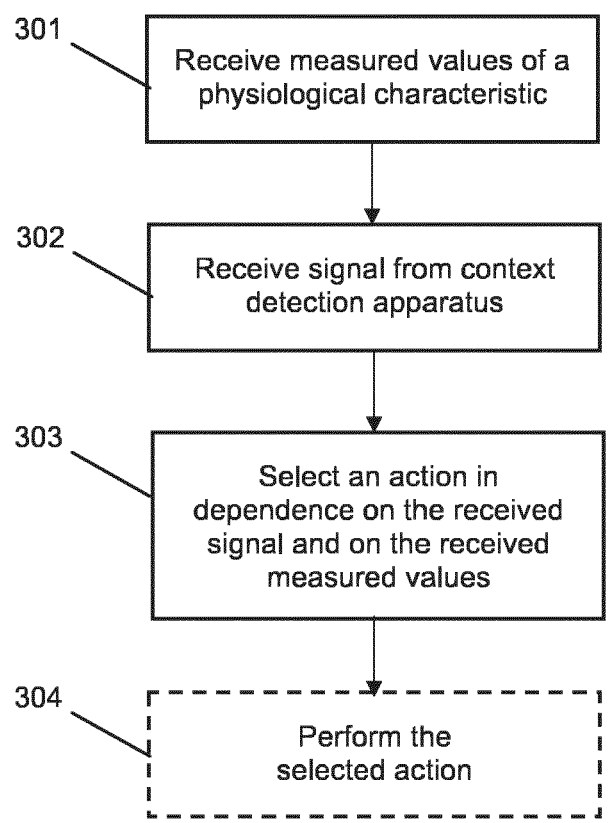
FIG. 3 is a flow chart illustrating a method performed by a medical monitoring device, according to a general embodiment of the invention.

FIG. 3 shows an example of a method performed by a medical monitoring device upon receiving a signal from a context detection apparatus, e.g. the signal output in step 203 of FIG. 2. In step 301 the medical monitoring device receives measured values of a physiological characteristic from a sensor connected to the medical monitoring device.

In some embodiments the measured values are received by an alarm generation module of the medical monitoring device. In step 302 the medical monitoring device receives a signal based on context information generated by a context detection apparatus (hereafter referred to as the "context signal"), e.g. from the context detection apparatus 1. In some embodiments the context signal is received by an alarm generation module of the medical monitoring device. In other embodiments the context signal is received by an alarm handling module of the medical monitoring device. It will be appreciated that steps 301 and 302 can occur simultaneously.

In some embodiments, i.e. embodiments in which the received context signal does not contain relevance information, the method includes the additional step of generating relevance information based on the received context signal. In such embodiments, preferably the context signal contains the one or more types of context information generated by the context detection apparatus. In such embodiments relevance information may be generated using a process which is the same as or similar to the process described above in relation to the operation of the context detection apparatus 1.

In step 303, the medical monitoring device selects an action to perform. The action is selected in dependence on the context signal. In some embodiments the action is selected in dependence on the context signal and on relevance information generated by the medical monitoring device. In some embodiments selecting an action in dependence on the received signal comprises the alarm generation module determining whether or not to generate an alarm based on the received measured values and on the received signal (and, optionally, on relevance information generated by the medical monitoring device). In some such embodiments the determining comprises assessing whether the received measured values meet at least one predefined alarm generation criterion. In some such embodiments the determining comprises assessing whether the received context signal is relevant to the received measured values, e.g. on the basis of relevance information contained in the context signal or generated by the medical monitoring device.

In some embodiments the action is selected from a set comprising one or more of:
generating an alarm;
not generating an alarm;
altering an alarm generation criterion;
altering a parameter relating to the emission of a generated alarm;
redirecting a generated alarm;
suppressing a generated alarm;
generating a context-related alarm
discarding or ignoring one or more measured values of a physiological characteristic (e.g. measurements acquired contemporaneously with context information relevant to those measurements);
flagging one or more measured values of a physiological characteristic as potentially unreliable or invalid;
applying a correction to one or more measured values of a physiological characteristic;
generating a message to a caregiver based on the content of the received signal;
repeating a previously performed measurement.

A context-related alarm is an alarm which indicates that relevant context information has been generated. In some embodiments a context-related alarm comprises a message to a caregiver, e.g. a caregiver whose responsibilities include dealing with context-related alarms. In some embodiments the context-related alarm includes the generated context information. In some embodiments the context-related alarm includes the context data on which the generated context information is based. In some embodiments the context-related alarm includes relevance information associated with the context information. In some embodiments the context-related alarm includes confidence information associated with the context information. In some embodiments the context-related alarm includes time information associated with the context information.

In some embodiments the action is performed in respect of measurements of a physiological characteristic which were obtained at or close to the time at which the context data used to generate the context information was obtained.

The method optionally includes a further step 304 of performing the selected action. In some embodiments the selected action is performed by the medical monitoring device. In some embodiments the medical monitoring device causes a further device, such as a remote alarm generation device, to perform the selected action.

Figure 4:
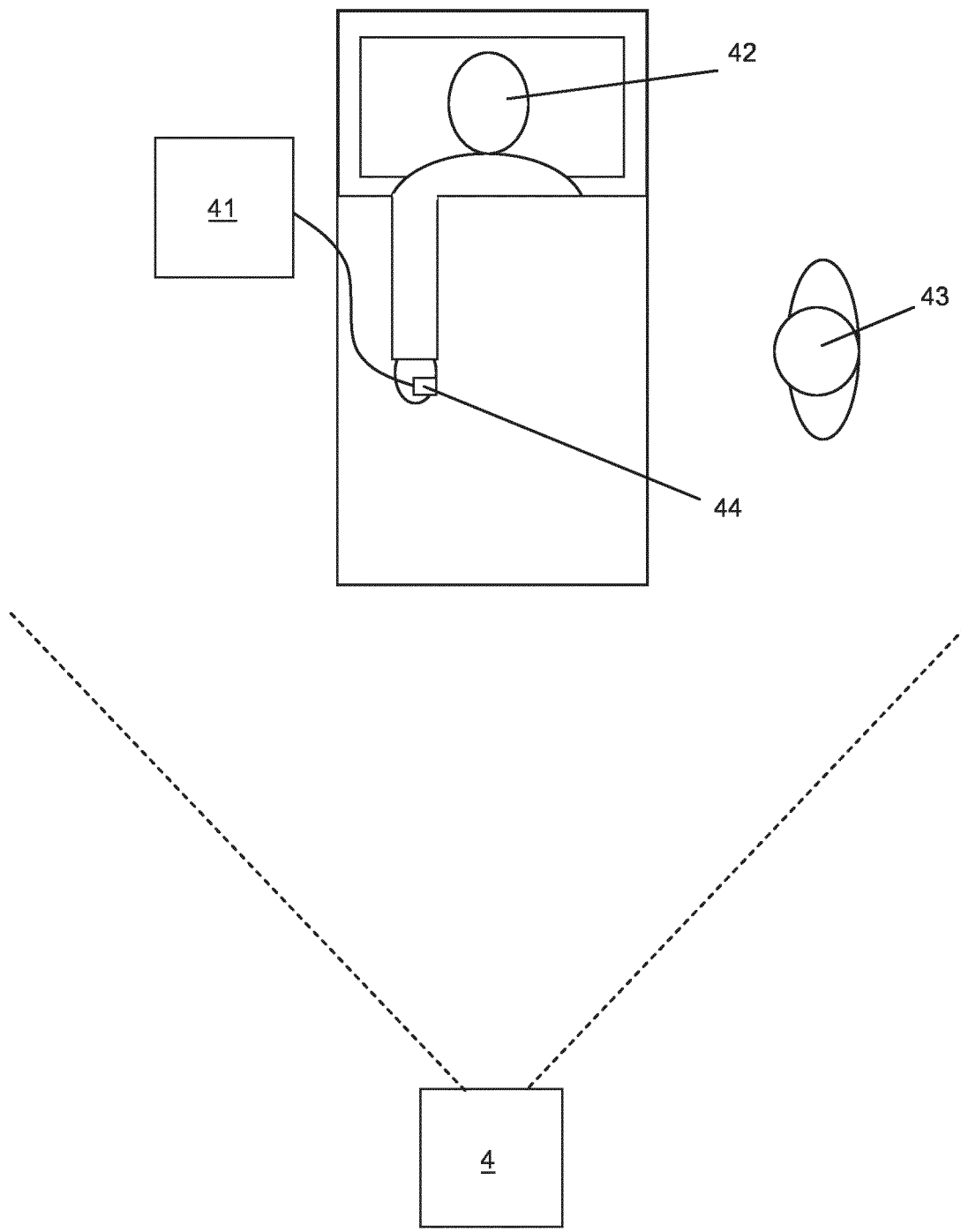
FIG. 4 is an illustration of a context-aware medical monitoring system according to a first specific embodiment of the invention.

A specific embodiment of the invention in which the context detection apparatus comprises a camera-based context detection apparatus 4 will now be described with reference to FIG. 4. FIG. 4 shows a subject 42 lying in a bed, which may be located for example in a hospital ward. A medical monitoring device 41 is provided next to the subject 42, and is connected to various sensors which are each arranged to detect a physiological characteristic of the subject. In this example the sensors include a PPG sensor (e.g. a finger-mounted pulse oximeter) 44 for acquiring PPG measurements and a heart rate sensor (not shown). Other sensors which might typically be used by a medical monitoring device include ECG sensors, $SpO_2$ sensors, blood pressure sensors, temperature sensors, and respiration rate sensors. A person 43 is shown standing in the vicinity of the subject. The context detection apparatus 4 comprises a camera (not shown) arranged such that the subject 42 and their immediate surroundings are within the field of view (FOV) of the camera (represented by the dashed lines in FIG. 4). For example in some embodiments the context detection apparatus 4 is mounted to a ceiling or high up on a wall. The context detection apparatus 4 also comprises a processing unit (not shown), which is arranged to receive image data from the camera.

In some embodiments the camera is arranged to continuously record and send image data to the processing unit in real-time or near real-time. However, alternative embodiments are possible in which the camera is arranged to periodically capture (and transmit) image data at a predetermined frequency, for example once per second. In some embodiments the camera is arranged to capture image data having a resolution of at least 1024×768 pixels. In preferred embodiments the camera is a high-resolution camera arranged to capture image data having a resolution significantly higher than 1024×768 pixels. In some embodiments the camera is a 3D camera. In some embodiments the camera is a wide-angle camera. In some embodiments the camera is an infrared (IR) camera or includes an IR channel. In some such embodiments the camera includes an IR illumination unit. Although FIG. 4 shows a single camera, alternative embodiments are envisaged in which a plurality of separate cameras are provided, e.g. to enable a larger field of view.

In some embodiments the processing unit has some or all of the features described above in relation to the processing unit 12 of the FIG. 1 embodiment. Additionally, the processing unit of the camera-based context detection apparatus 4 comprises a video analysis system. The processing unit is arranged to use the video analysis system to analyze the image data received from the camera. In some embodiments the video analysis system is arranged to:

detect a feature of interest in the image stream;
    determine one or more properties of a detected feature;
    compare the one or more determined properties to at least one predefined criterion; and
    set one or more context flags based on the results of the comparison.

These processes may be performed by the video analysis system using any suitable video analysis techniques known in the art.

Motion is known to affect PPG signals recorded by a finger-clip sensor. For example, if the sensor moves parallel to the direction of the digital arteries, the PPG signal becomes sinusoidal-shaped, whereas if the direction of motion is orthogonal to the digital arteries, the PPG signal contains more short, sharp, edgy motion artifacts. Motion parallel to the direction of the digital arteries is expected to more severely affect SpO2 accuracy.

Figure 5:
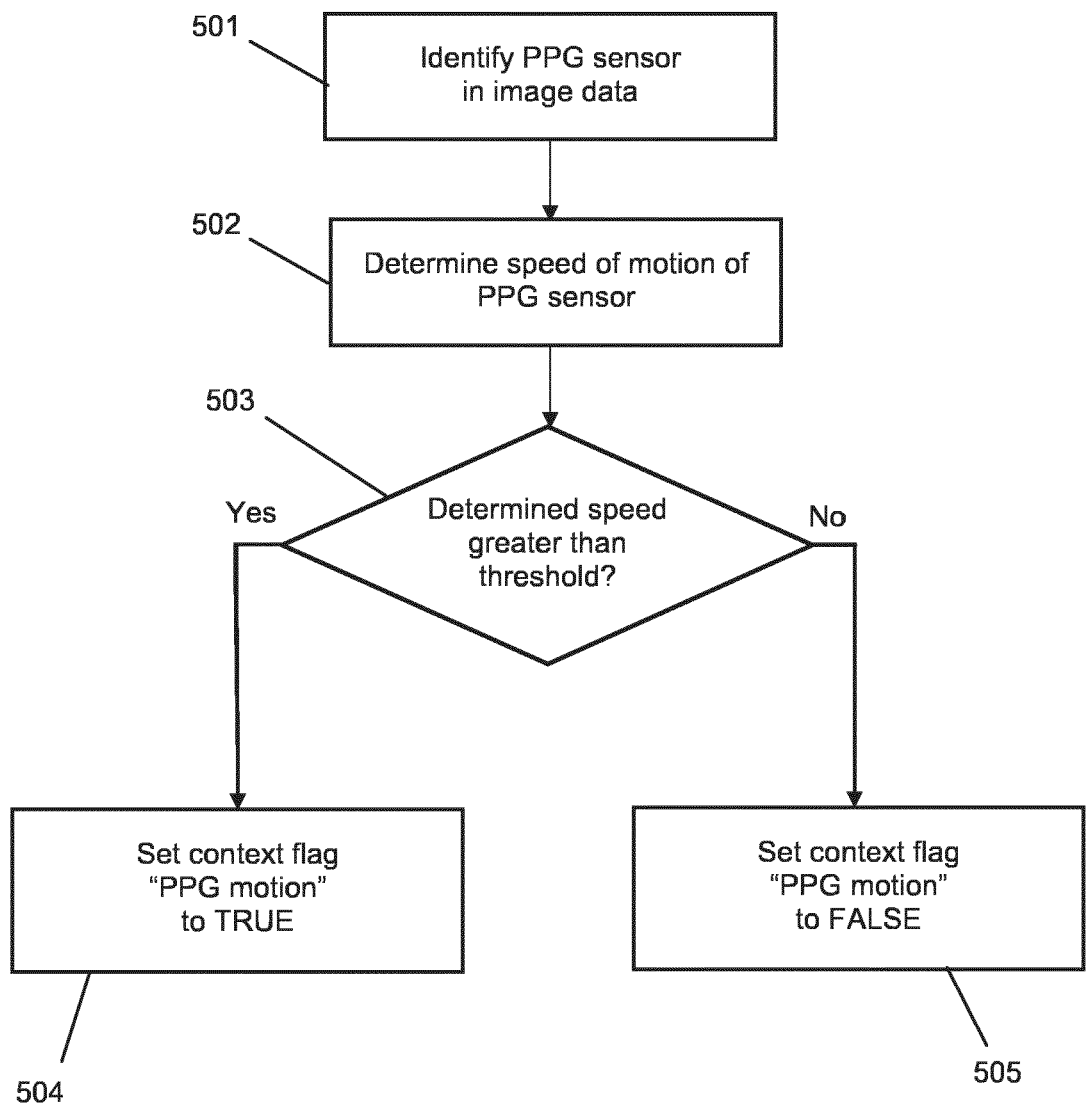
FIG. 5 is a flow chart illustrating a first process performed by a context detection apparatus of the medical monitoring system of FIG. 3.

Since subjects frequently move their hands (e.g. to make gestures or reach for things), the context detection apparatus 4 is arranged to detect and flag motion of the PPG sensor 44 using the process shown in FIG. 5. In a first step 501 the PPG sensor is identified in the received image data. The PPG sensor 44 is defined as a feature of interest for the purposes of the video analysis system (e.g. by way of a predefined pattern, signature, shape, or set thereof stored in a memory of the processing unit). For example, PPG sensors typically include red and IR LEDs, so a criterion used in identifying a PPG sensor in the image data might be the presence of a small bright red area. The video analysis system is thereby able to detect the PPG sensor in the received image stream (e.g. using edge detection, shape recognition, color detection, or any other suitable image analysis techniques). In some embodiments in performing step 501 the video analysis system detects the PPG sensor 44 in all frames of the received image data. In some embodiments the video analysis system detects the PPG sensor 44 at regular intervals, e.g. in every other frame. Since each image frame is associated with a time at which it was captured, the video analysis system can thereby track the position of the PPG sensor 44 over time. This allows one or more properties of the motion of the PPG sensor at any given time (e.g. position, orientation, speed, direction, acceleration, distance traveled, etc.) to be calculated by the processing unit.

In step 502 the video analysis system determines a speed of motion of the PPG sensor 44. It will be appreciated that image data covering a time period is required in order for the speed to be determined (although this the time period may be as small as the time between two consecutive frames), and that the determined speed will be an average over that time period. In some embodiments step 502 is performed at predetermined time intervals, e.g. once per second. Preferably the length of the predetermined time intervals is in the range 0.1-2 seconds. Preferably the length of the predetermined time intervals is less than the duration of a typical cardiac cycle.

In step 503, each speed value output by step 502 is compared to a predefined threshold. The value of the predefined threshold is set such that sensor movements equal to or slower than the threshold are unlikely to significantly affect the measured PPG values, whereas sensor movements faster than the thresholds are likely to affect the measured PPG values. Preferably the threshold value is less than 1 m/s. In some embodiments the threshold value is 0.02 m/s. If the result of the comparison is that the determined speed is greater than the predefined threshold, then in step 504 the value of a context flag entitled "PPG motion" is set to TRUE. If, on the other hand, the result of the comparison is that the determined speed is less than or equal to the predefined threshold, then in step 505 the value of the context flag entitled "PPG motion" is set to FALSE. Thus, a PPG motion context flag having a value of either TRUE or FALSE is generated at regular intervals (i.e. a flag is generated, or a previously generated flag is updated, for each speed determination made in step 502).

It will be appreciated that other types of context information will also be relevant to the PPG measurements, and that PPG context flags can additionally be generated in respect of such other types of context information. For example, ambient light (in particular modulated or "coded" light) is a potential source of interference for a PPG sensor. It can be determined from the image data whether modulated ambient light is present in the area where the PPG is located. Thus in some embodiments a context flag entitled "PPG modulated light" is generated at regular intervals (or is generated and then updated at regular intervals.

Figure 6:
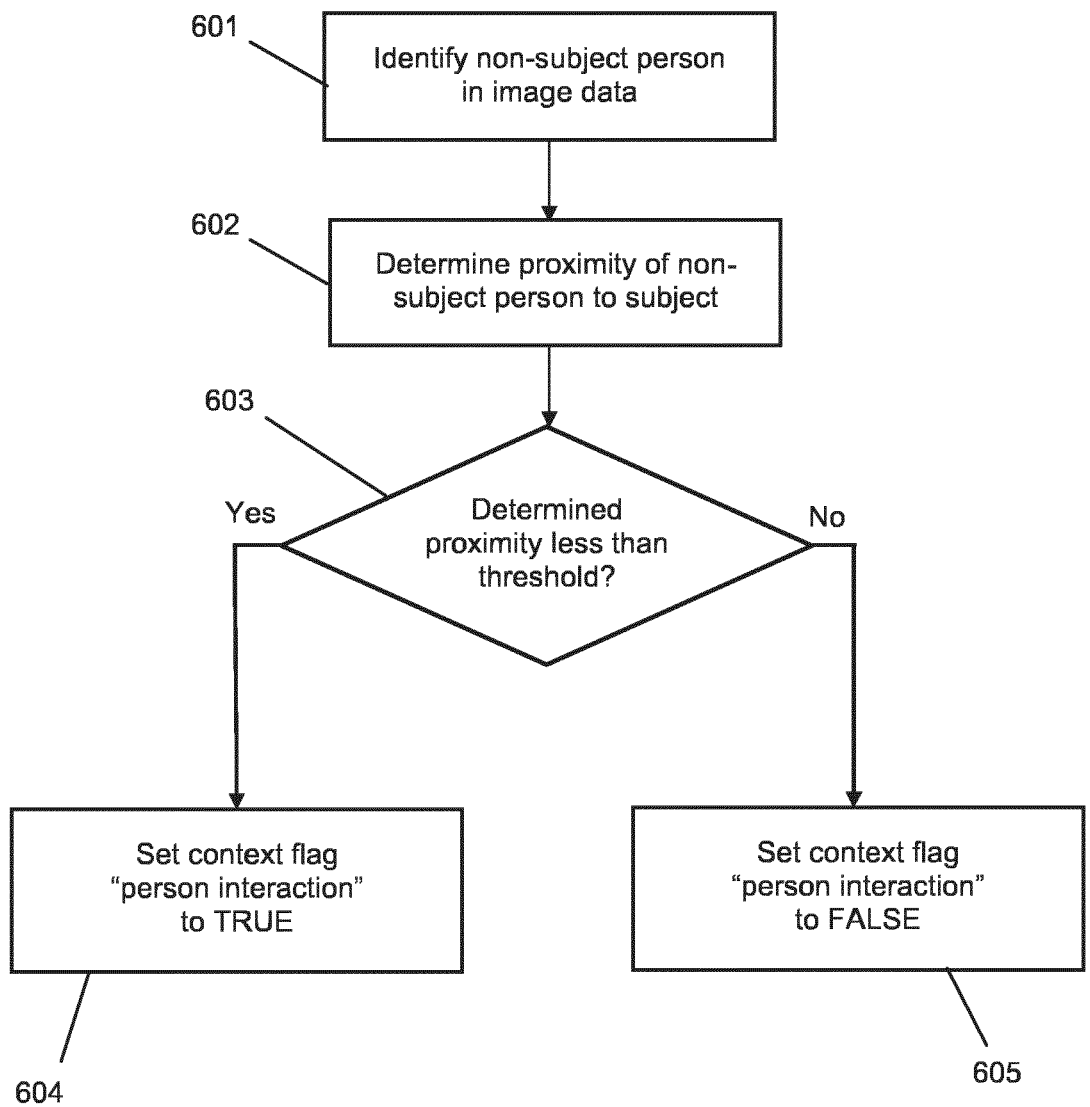
FIG. 6 is a flow chart illustrating a second process performed by a context detection apparatus of the medical monitoring system of FIG. 3.

Measurements of some physiological characteristics are also known to be affected as a result of a caregiver interacting with the subject. For example, a caregiver entering the subject's room may result in slight elevation of heart rate and blood pressure, and painful interactions (e.g. needle insertion) can invoke even stronger physiological responses. These kinds of responses are typically not relevant clinically, so it is advantageous to avoid alarms being generated as a result of such responses. The context detection apparatus 4 is therefore arranged to detect and flag the presence of a caregiver 43 in the vicinity of the subject 42, using the process shown in FIG. 6.

In step 601 a person 43 other than the subject 42 is identified in the received image data. A non-subject person is defined as a feature of interest for the purposes of the video analysis system. Entering of a non-subject person into the FOV of the camera can be detected in the image data stream by, e.g., detecting a change at the image borders compared to a computed background model. Departure of the non-subject person from the FOV can be detected in a similar manner. Characteristic features (such as shape, color, etc.) of a detected non-subject person 43 can be stored by the video analysis system to allow the non-subject person 43 to be detected in subsequent frames of the image data. In some embodiments in performing step 601 the video analysis system seeks to detect an identified non-subject person 43 in all frames (during which the non-subject person 43 is in the FOV) of the received image data. In some embodiments the video analysis system detects the non-subject person 43 at regular intervals, e.g. in every other frame. Since each image frame is associated with a time at which it was captured, the video analysis system can thereby track the position of the non-subject person over time.

In some embodiments the type (e.g. caregiver, family member) or specific identity of the non-subject person is determined, e.g. using face recognition techniques, or analyzing other features of the non-subject person 43 such as clothing color. It will be appreciated that a caregiver in close proximity to the subject is likely to be performing procedures on the subject (e.g. washing or moving the subject, taking a blood sample, performing an examination, etc.), and therefore that a non-clinically relevant influence on measured physiological characteristics is more likely to occur if the non-subject person is a caregiver than if the non-subject person is a family member or friend. As such, in some embodiments an additional step of determining whether or not the non-subject person is a caregiver is performed.

In step 602 the video analysis system determines a proximity of the non-subject person 43 to the subject 42, using any suitable image analysis techniques known in the art. In some embodiments the proximity determination is performed continuously, for every frame of the image data. In some embodiments step 602 is performed at predetermined time intervals, e.g. once per second. Preferably the length of the predetermined time intervals is in the range 0.1-2 seconds. Preferably the length of the predetermined time intervals is less than the duration of a typical cardiac cycle.

In step 603, each proximity value output by step 602 is compared to a predefined threshold. The value of the predefined threshold is set such that non-subject persons greater than the threshold distance away from the subject are unlikely to significantly affect the measured values of particular physiological characteristic. In some embodiments in which a determination is made as to whether the non-subject person is a caregiver, different thresholds are defined in respect of caregivers and non-caregivers. It will be appreciated that other categories of person can be defined, and that separate thresholds can be provided in respect of each different defined category.

In some embodiments a predefined proximity threshold is defined for each different type of physiological characteristic measured by the medical monitoring device 41. PPG values, for example, are less likely to be affected by the proximity of a non-subject person than heart rate values, so in some embodiments a relatively low proximity threshold is defined for PPG measurements and a relatively high proximity threshold is defined for heart rate measurements. If the result of the comparison is that the determined proximity is less than the predefined threshold, then in step 604 the value of a context flag entitled "person interaction" is set to TRUE. If, on the other hand, the result of the comparison is that the determined proximity is greater than or equal to the predefined threshold, then in step 605 the value of the context flag entitled "person interaction" is set to FALSE. Thus, a person interaction context flag (or a set of person interaction context flags for each of multiple measured physiological characteristics) having a value of either TRUE or FALSE is generated at regular intervals, or is generated and continuously updated.

A signal containing all of the generated context flags (i.e. including the PPG context flags, the person interaction context flags, and any other context flags generated by the context detection apparatus 3) is sent from the context detection apparatus 3 to the medical monitoring device 41, either continuously or at regular intervals. (It will be appreciated that the determined speed of the PPG sensor comprises a particular type of "context information" as described above in relation to FIG. 1, as does the determined proximity of a non-subject person, and that the PPG motion context flags and the person interaction context flags are based on the determined speed and the determined proximity respectively. The signal is therefore based on generated context information, in the sense of the FIG. 1 embodiment).

The medical monitoring device 41 comprises a processing unit which includes an alarm generation module and an alarm handling module. The alarm generation module is arranged to receive physiological characteristic measurements from the variety of sensors. In some embodiments the alarm generation module is also arranged to receive a signal from the context detection apparatus 4. The alarm generation module is further arranged to determine whether or not an alarm is to be generated based on the received measurements (and, if applicable, the signal received from the context detection apparatus). In some embodiments the alarm generation module is arranged to determine whether or not an alarm is to be generated in respect of one or more different alarm types. In the event that the alarm generation module determines that an alarm is to be generated, it generates the appropriate alarm by outputting a signal to the alarm handling module.

In a particular example the received measured values comprise PPG measurements and heart rate measurements and the received context signal contains PPG motion context flags and person interaction context flags (it will be appreciated that additional types of measured values and types of context information may also be being received). In this example the alarm generation module is programmed to check PPG motion context flags but not to check person interaction context flags when determining whether or not to generate an alarm based on received PPG measurements; and when determining whether or not to generate an alarm based on received heart rate measurements is programmed to check person interaction context flags but not PPG motion context flags.

Thus, when processing received PPG measurements, the alarm generation module checks the values of the PPG motion context flags received in the signal from the context detection apparatus. If the received signal contains one or more PPG motion context flags with the value TRUE, then in some embodiments the alarm generation module ignores received measured values which were acquired during the time period(s) corresponding to the TRUE-valued context flags (e.g. by flagging them as invalid and not using them in the determination of whether to generate an alarm). In other embodiments the alarm generation module does not ignore received measured values which were acquired during the time period(s) corresponding to the TRUE-valued context flags, but instead applies a different alarm generation criterion in respect of these measured values. In some embodiments the alarm generation module is programmed to check multiple types of context information (e.g. PPG motion context flags and a further type of context flags) in relation to, e.g., received PPG measurements. In such embodiments the alarm generation module ignores (or applies a different alarm generation criterion to) received measured values which were acquired during the time period(s) corresponding to all of the TRUE-valued context flags, regardless of context type.

The alarm generation module then assesses whether the received PPG measurements meet an alarm generation criterion (such as exceeding a threshold for more than a predefined amount of time). As discussed above, in some embodiments only the valid measurements are used in this assessment. In other embodiments all measurements are used but a different alarm generation criterion is applied (e.g. a higher PPG threshold) to measurements which were acquired during the time period(s) corresponding to the TRUE-valued context flags. In such embodiments the selected action comprises altering an alarm generation criterion. If the measurements meet the alarm generation criterion, the alarm generation module generates an alarm by outputting an alarm signal to the alarm handling module. The selected action therefore comprises generating an alarm. Alternatively, if the alarm generation criterion was not met, the selected action would comprise not generating an alarm and/or waiting to receive further measured values. In some embodiments, the alarm generation module is arranged to, alternatively or additionally, generate a context alarm when the received signal meets at least one predefined context alarm criterion. For example, the alarm generation module may be arranged to generate a context alarm when a predefined minimum number of consecutive TRUE-valued context flags of a particular type is received. In such embodiments the selected action would comprise generating a context alarm.

When processing received heart rate measurements, the alarm generation module checks the values of the person interaction context flags received in the signal from the context detection apparatus 3. If the received signal contains one or more person interaction context flags with the value TRUE, then in some embodiments the alarm generation module ignores received measured values which were acquired during the time period(s) corresponding to the TRUE-valued context flags (e.g. by flagging them as invalid and not using them in the determination of whether to generate an alarm). In other embodiments the alarm generation module does not ignore received measured values which were acquired during the time period(s) corresponding to the TRUE-valued context flags, but instead applies a different alarm generation criterion in respect of these measured values. As when assessing PPG measurements, in some embodiments the alarm generation module is programmed to check multiple types of context information (e.g. person interaction context flags and a further type of context flags) in relation to received heart rate measurements.

The alarm generation module then assesses whether the received heart rate measurements meet an alarm generation criterion. As discussed above, in some embodiments only the valid measurements are used in this assessment. In other embodiments all measurements are used but a different alarm generation criterion is applied (e.g. a higher heart rate threshold) to measurements which were acquired during the time period(s) corresponding to the TRUE-valued context flags. If the measurements meet the alarm generation criterion, the alarm generation module generates an alarm as described above in relation to the processing of PPG measurements.

The alarm handling module is arranged to receive signals from the alarm generation module. In some embodiments (i.e. embodiments in which the alarm generation module is not arranged to receive a signal from the context detection apparatus 4) the alarm handling module is also arranged to receive a signal from the context detection apparatus 4. In some embodiments the alarm handling module is also arranged to receive alarm signals from the point of care devices. The alarm handling module is arranged to cause an alarm generated by the alarm generation module (or by a point of care device) to be emitted, e.g. by displaying a message on a screen, activating a loudspeaker, activating a warning light, sending a signal to a remote alarm emitting device, and/or sending a signal to a portable device belonging to a caregiver. In embodiments in which the alarm handling module is arranged to receive a signal from the context detection apparatus 4, the alarm handling module is further arranged to determine whether or not to suppress a generated alarm based on the received signal. Suppressing an alarm may comprise, for example, not causing an alarm generated by the alarm generation module to be emitted, or altering a parameter relating to the alarm, e.g. by selecting a different modality to emit the alarm, redirecting the alarm to a different caregiver device, and/or altering information comprised in the alarm.

Embodiments of the invention therefore advantageously enable the number of false alarms generated by a medical monitoring device to be reduced. Furthermore, particular embodiments can facilitate more detailed and accurate interpretation of measured values by a medical monitoring system, enabling the possibility of increased automation in diagnosis and treatment of a monitored subject. Embodiments of the invention therefore have the potential to significantly reduce the burden on caregivers.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for use in monitoring a physiological characteristic of a subject using a medical monitoring device, the method comprising:
   receiving a single type of sensor data acquired by at least one context sensor;
   analyzing, by a processing unit, the received single type of sensor data by detecting features in the received single type of sensor data and classifying each detected feature as relating to a particular type of a plurality of different types of context information, wherein each type of context information comprises information which relates to a factor capable of influencing measured values of the physiological characteristic and which is not measurable by the medical monitoring device, and the generated context information comprises one or more of information relating to the movement of a body part of the subject, information relating to the posture of a subject, information relating to the activity of a subject, information relating to the location of a subject, information relating to one or more persons in the vicinity of the subject, and information relating to the environment of the subject;
   comparing each type of generated context information to at least one predefined criterion comprising a set of conditions, which must all be met by a given item of context information in order for a positive relevance value to be assigned to that context information:
   assigning a relevance value to each type of generated context information based on the comparing step; and
   outputting via a communication functionality of the processing unit a context signal to the medical monitoring device based on the generated context information.

2. The method of claim 1, further comprising:
   measuring multiple physiological characteristics using the medical monitoring, wherein the at least one predefined criterion is specific to a particular type of context information and to a particular physiological characteristic, and wherein assigning the relevance value to each type of generated context information further comprises:

assigning the relevance value in respect of each of the multiple physiological characteristics to each type of generated context information.

3. A method according to claim 1, further comprising:

receiving, by the medical monitoring device, measured values of a physiological characteristic from a sensor;

receiving, by the medical monitoring device, the context signal; and selecting, by the medical monitoring device, an action to perform, wherein the action is selected in dependence on the received context signal and on the received measured values.

* * * * *